United States Patent [19]

Kamaya et al.

[11] Patent Number: 5,106,179
[45] Date of Patent: Apr. 21, 1992

[54] EYESIGHT AUXILIARY LIQUID CRYSTAL DEVICE

[75] Inventors: Naoki Kamaya, Tokyo; Seizi Sato, Kanagawa, both of Japan

[73] Assignee: Sony Corporation, Japan

[21] Appl. No.: 697,208

[22] Filed: May 8, 1991

[30] Foreign Application Priority Data

May 17, 1990 [JP] Japan ................................. 2-128007

[51] Int. Cl.⁵ .............................................. G02C 1/00
[52] U.S. Cl. ...................................... 351/158; 351/44
[58] Field of Search ................ 351/41, 44, 45, 46, 351/47, 48, 49, 158, 206, 207, 208; 359/41, 57, 58, 64, 66, 67, 68, 84, 85; 2/432

[56] References Cited

U.S. PATENT DOCUMENTS 4,848,890 7/1989 Horn ................................. 351/158

Primary Examiner—Rodney B. Bovernick
Attorney, Agent, or Firm—Ronald P. Kananen

[57] ABSTRACT

An eyesight auxiliary device having within a main body of the device is described, a spot light source, transparent liquid cyrstal panels illuminated by the spot light source and convex lenses substantially integrally arranged with the liquid crystal panels. The main body of the device is fitted to a user's head, the image of the liquid crystal panels is directly projected onto the retina of the user's eyeballs through the spot light source. Further, a small-sized camera for capturing the image of the liquid crystal panels is arranged at a position corresponding to the height positions of the eyeballs.

6 Claims, 5 Drawing Sheets

BLOCK DIAGRAM FOR IMAGE DISPLAYING CIRCUIT

EYESIGHT AUXILIARY LIQUID CRYSTAL DEVICE

BACKGROUND OF THE INVENTION

1. Field of the Invention

This invention relates to an eyesight auxiliary device which is suitable for a person with catarcts or amblyopia.

2. Description of the Prior Art

In recent years, an increasing number of people have been diagnosed as suffering from cataracts or amblyopia. People suffering from cataracts or amblyopia wear glasses to correct their eyesight.

SUMMARY OF THE INVENTION

This invention provides an eyesight auxiliary device in which a spot light source, transparent liquid crystal panels illuminated by the spot light source, and short focusing convex lenses substantially integral with the liquid crystal panels are arranged within a main body of the device. Further the main body of the device is fitted to a user's head and images of the liquid crystal panels are directly projected onto the retina of the user's eyeballs through the spot light source. A small-sized camera capturing the images of the liquid crystal panels is in the main body of the device at a position corresponding to the heights of the eyeballs. Thereby, the images captured by the small-sized camera and projected onto the liquid crystal panels can be projected directly onto retina of the eyeballs through the spot light source and thus a clear image can be obtained independent of the viewer's eyesight.

However, a person with cataracts or amblyopia hardly corrects his or her eyesight by wearing glasses (in particular, a person with cataracts has his or her pupil clouded and eyesight is not improved even by wearing glasses) and the eyesight is lost, badly affecting the daily life of such a person with cataracts.

In view of this fact, the present invention provides an eyesight auxiliary device capable of helping the eyesight of of a person with cataracts or amblyopia.

This eyesight auxiliary device is comprised of a spot light source, transparent liquid crystal panels illuminated by the spot light source, and convex lenses substantially integrally arranged with the liquid crystal panels. The main body of the device is fitted to the user's head, the images of the liquid crystal panels are directly projected the retina of a eyeballs through the spot light source, and the smallsized camera for taking the images of the liquid crystal panels is arranged in the main body of the device at the height positions corresponding to the eyeballs.

The images taken by the small-sized camera and projected onto the transparent liquid crystal panels are projected with the spot light source and directly projected onto the retina of the eyeballs through the convex lenses. With such an arrangement, a clear image can be seen independent of the viewer's eyesight.

DESCRIPTION OF THE PREFERRED EMBODIMENTS

Figure 1:
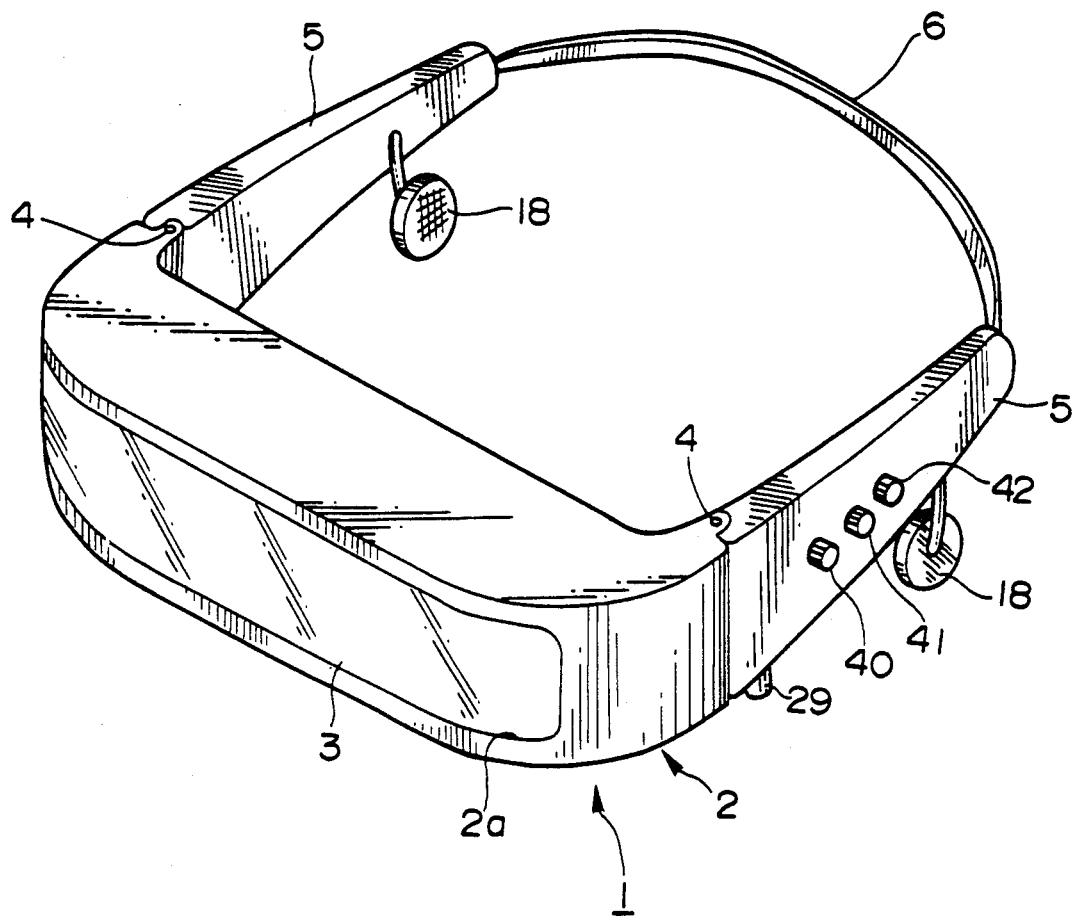
FIG. 1 is a perspective view of an eyesight auxiliary device for illustrating one preferred embodiment of the present invention.

Referring now to the drawings, one preferred embodiment of the present invention will be described.

Figure 5:
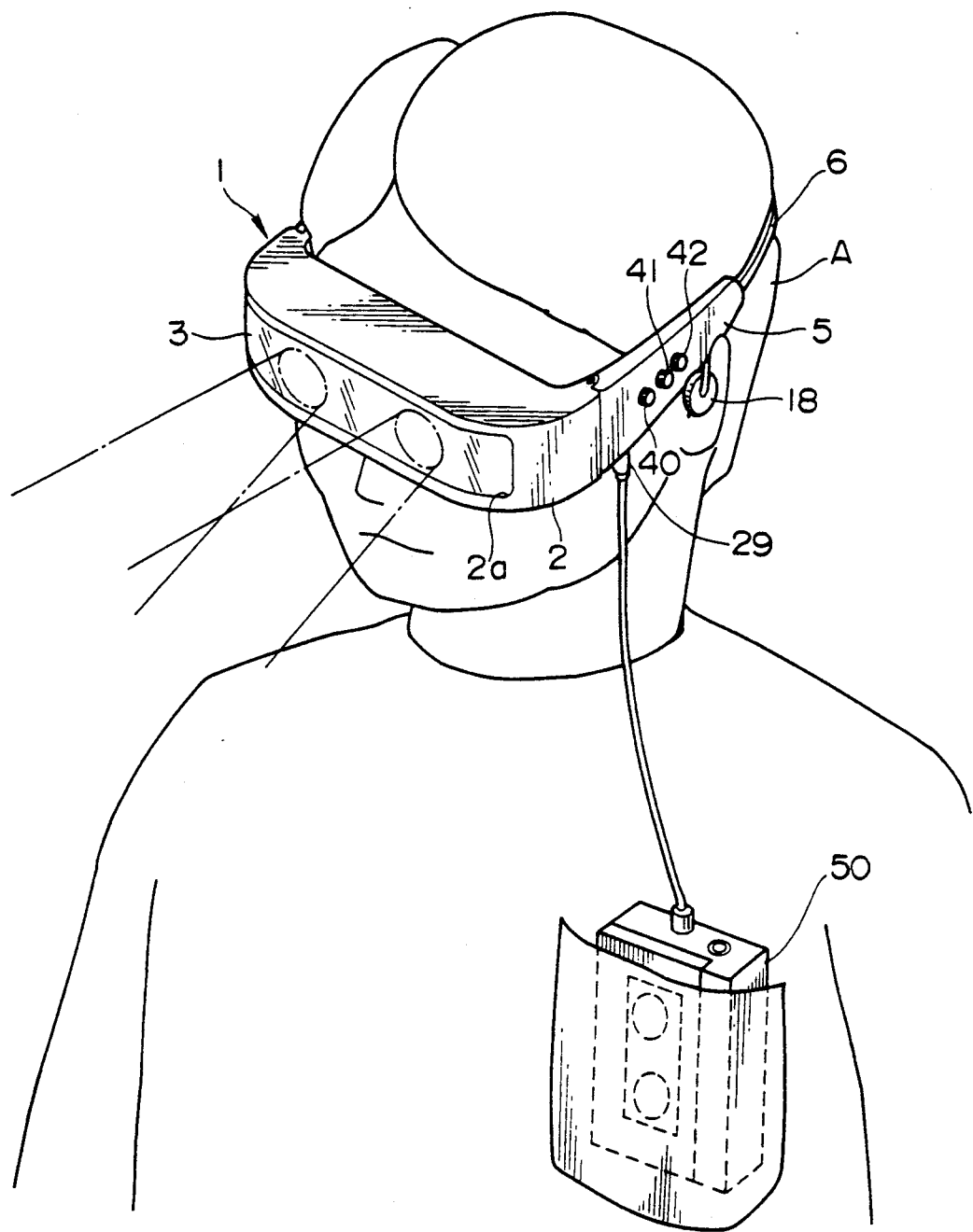
FIG. 5 is a perspective view for showing a state of use of the device.

In FIGS. 1 and 5, reference numeral 1 denotes an eyesight auxiliary device of an eye glasses type and the main body 2 of the device is formed like ski glasses, for instance. A window portion 2a opened in a substantial rectangular shape at a front portion of the main body 2 of the device is covered by a transparent plate 3. A pair of side frames 5 are supported at both rear end edges of the main body 2 of the device in such a way that they may be folded. When the main body 2 of the device is fitted to the head A of the user by means of a rubber belt 6 of which both portions are fixed at the rear ends of the pair of side frames 5, respectively, the eyesight auxiliary device 1 may not be easily disengaged by the weight of the main body 2 of the device and the device can be used as glasses.

Figure 2:
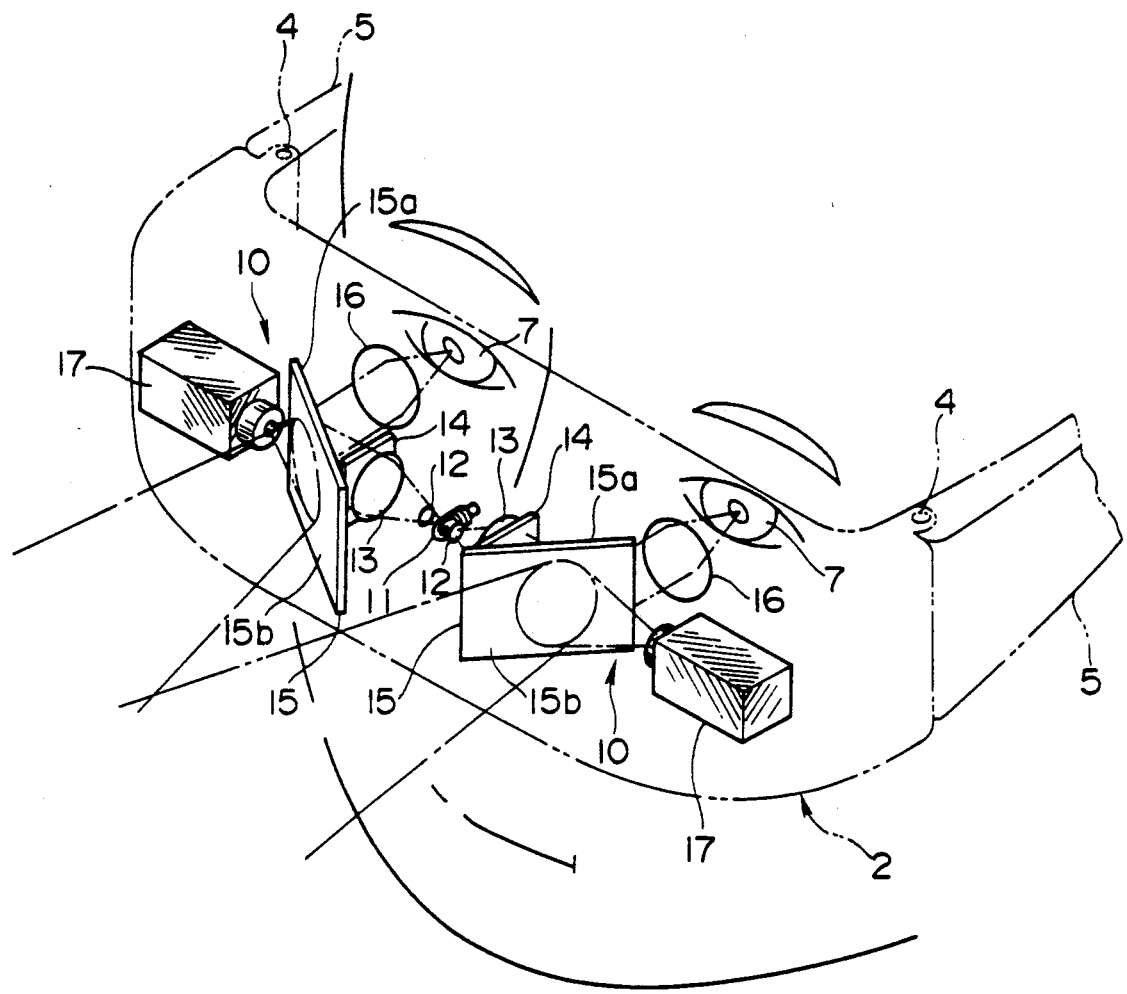
FIG. 2 is a perspective view illustrating an optical system for the liquid crystal panel of the device.
Figure 3:
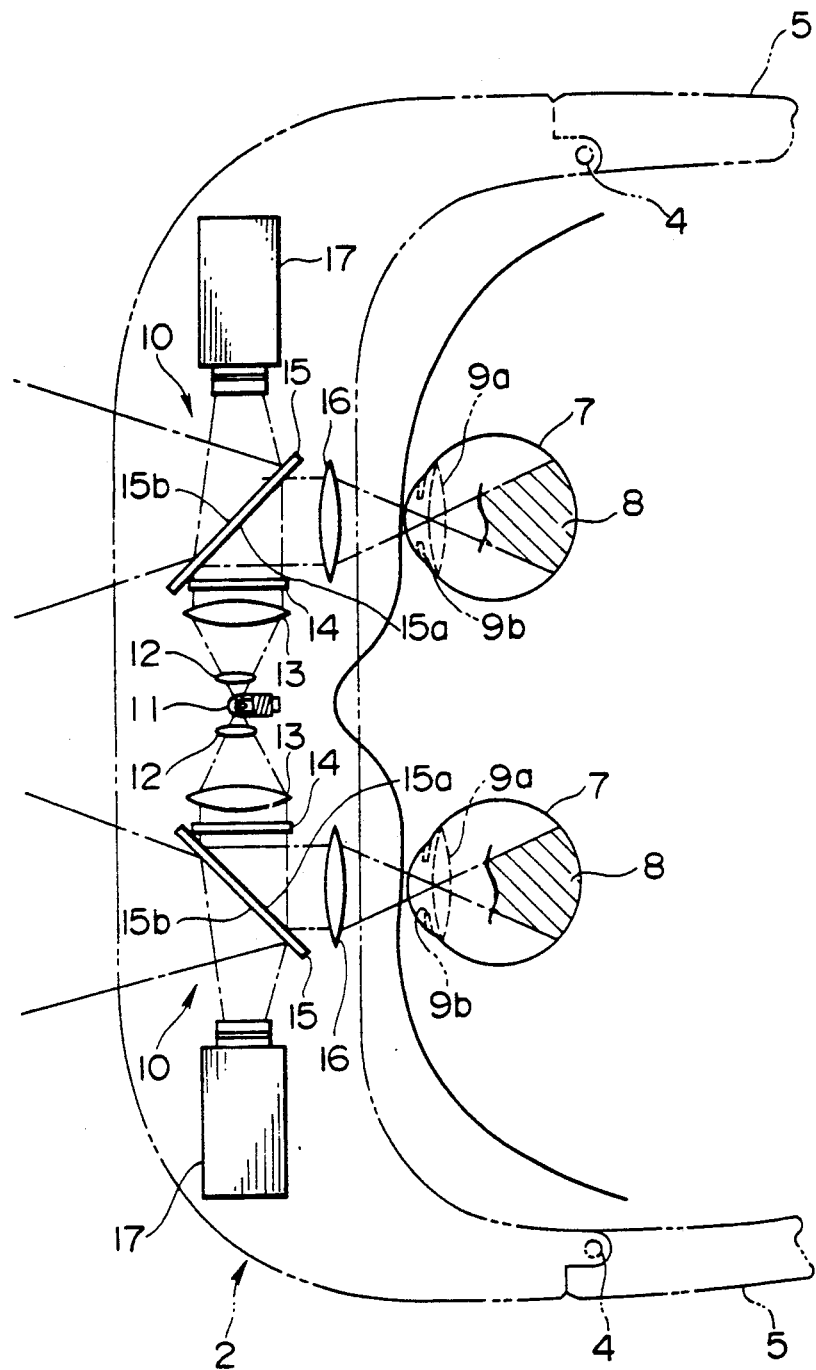
FIG. 3 is a top plan view of the optical system.

A pair of optical systems 10, best seen in FIG. 2, for displaying the image are arranged at positions within the main body 2 of the device corresponding to each of the right and left eyeballs 7. As shown in FIGS. 2 and 3, each of the optical systems 10 is substantially comprised of a miniature bulb (a spot light source) 11 arranged at a central portion within the main body 2 of the device; each of a pair of right and left small and large lenses 12 and 13 for focusing the light beam of the miniature bulb 11 toward both sides of the main body 2 of the device; each of transparent liquid crystal panels 14 are illuminated by the light beam of the miniature bulb 11 focused by each of a pair of lenses 12 and 13; each of mirrors 15 have both mirror surfaces arranged at positions corresponding to each of the eyeballs 7 so as to reflect the images of each of the liquid crystal panels 14 with first mirror surfaces 15a; each of short focusing convex lenses 16 are for focusing the images reflected by each of the mirrors 15 to each of the eyeballs 7; and each of wide view angle type small-sized video cameras 17 are arranged at positions corresponding to second mirror surfaces 15b of each of the mirrors 15, taking an image (an external sight or the like) viewed at the second mirror surface 15b of each of the mirrors 15 and projecting it to each of the liquid crystal panels 14. The small-sized video cameras 17, mirrors 15 and liquid crystal panels 14 can be moved integrally in a righthand or a lefthand direction by a moving mechanism not shown. The position of each of the mirrors 15 is aligned with the position of each of the right and left eyeballs 7, thereby the position of each of the small-sized video cameras 17 is also aligned with the position of each of the right and left eyeballs 7. An image captured by each of the small-sized video cameras 17 and projected by each of the liquid crystal panels 14 is projected directly to the retina 8 of each of the right and left eyeballs 7, respectively, by a spot light source of the miniature bulb 11. Reference numeral 9a in FIG. 3 denotes a crystalline lens of the eye and reference numeral 9b denotes a pupil.

Figure 4:
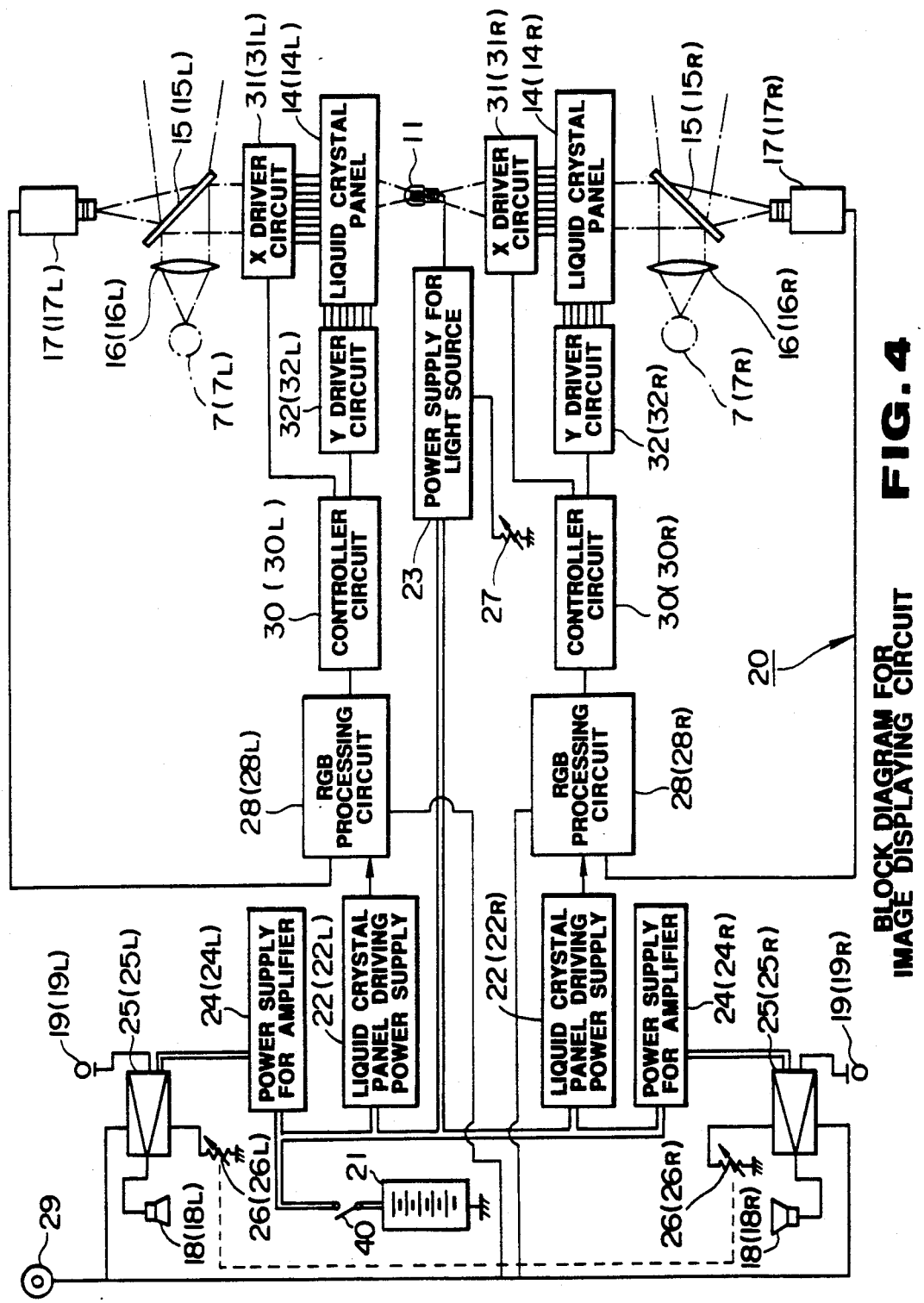
FIG. 4 is a block diagram of an image displaying circuit to be used in the device.

Head-phones 18 are fixed to inner central portions of each of the side frames 5. Referring to FIG. 4, one (left) of the side frames 5 stores an image displaying circuit 20. A configuration of the image displaying circuit 20 is shown in the block diagram of FIG. 4. This image displaying circuit 20 is substantially comprised of a battery 21 acting as a power supply for a liquid panel driving power supply 22 (22R, 22L), a light source power supply 23 and an amplifier power supply 24 (24R, 24L); an amplifier 25 (25R, 25L) for a microphone 19 (19R, 19L) is fixed at both sides of the main body 2 of the device as well as the head-phone 18 (18R, 18L); a variable resistor 26 (26R, 26L) cooperatively is connected to a power-/sound volume adjusting switch 40 projecting from a side surface of the left side frame 5; a liquid crystal brightness variable resistor 27 is cooperatively connected to a liquid crystal panel brightness adjusting knob 41 projecting from the side surface of the left side frame 5; and an image/sound input terminal 29 is provided for inputting an image signal from an external part of the VTR 50 to RGB process circuit 28 (28R, 28L) or inputting a sound signal from the external part of the VTR 50 to the head-phone 18 (18R, 18L).

An image signal from the small-sized video camera 17 (17R, 17L) or an image signal from the image/sound input terminal 29 is inputted to the RGB process circuit 28 (28R, 28L) and processed there. R (red), G (green) and B (blue) signals processed by this RGB process circuit 28 (28R, 28L) are inputted to a controller circuit 30 (30R, 30L) so as to drive the liquid crystal panel 14 (14R, 14L) through X driver circuit 31 (31R, 31L) and Y driver circuit 32 (32R, 32L), respectively. The miniature bulb 11 of a spot light source of the liquid crystal panel 14 (14R, 14L) is lit by the light source power supply 23. The miniature bulb is projected at the side surface of the left side frame 5 and temporarily turned OFF when a push-type muting button 42 connected to the light source power supply 23 and the amplifier 25 or the like is turned ON. In this case, the sound is also temporarily shut off.

According to the eyesight auxiliary device 1 of the preferred embodiment, a person with cataracts or amblyopia fits the main body 2 of the device one the head A by means of a pair of side frames 5 and a rubber belt 6 in the same manner as wearing glasses, thereafter the power/sound volume adjusting switch 40 is turned ON, the image of the external scene or the like taken by a pair of small-sized video cameras 17 are projected by a pair of right and left liquid crystal panels 14. The image projected by the pair of liquid crystal panels 14 is projected directly onto each of the right and left eyeballs 7 through each of the short focusing lenses 16. With such an arrangement, the user with a amblyopia may see a clear three dimensional image reagardless of the viewer's eyesight power. The light source for the liquid crystal panels 14 is applied by a spot light source of the miniature bulb 11; information is sent into the center of the pupils 9b to project it directly onto each of the right and left eyeballs 7, so that when a person with cataracts extending from a peripheral part of the pupil uses this device, a more clear image can be seen than that seen with bare eyes.

As shown in FIG. 5, the VTR 50 or the like can be connected to the image/sound input terminal 29 of the main body 2 of the device so as to input the video-/sound signals and then the TV screen can be seen in the same manner as that described above.

Each of the mirrors 15 is arranged in the main body 2 of the device at a position opposing each of the right and left eyeballs 7 and the image received at each of the mirrors 15 is viewed by each of the small-sized video cameras 17 installed at the same position as the height position of each of the eyeballs 7, so that the same image as that directly seen with each of the eyeballs 7 can be directly seen at the retina 8 of each of the eyeballs 7 through each of the small-sized video cameras 17 and each of the liquid crystal panels 14 or the like. At this time, since each of the mirrors 15 is used, the image taken by each of the small-sized video cameras 17 and the image projected by each of the liquid crystal panels 14 are inverted at their right side and left side, respectively. However, the image projected by each of the liquid crystal panels 14 is reversed again by each of the mirrors 15, so that an image having the same orientation as that of the image seen by each of the right and left eyeballs 7 can be seen. In this case, since the position of each of the mirrors 15 can be adjusted to that of each of the right and left eyeballs 7, a three dimensional view feeling may not be varied.

Since the image captured by the small-sized video cameras 17 and the image projected by the liquid crystal panels 14 are reflected by a single mirror, the main body 2 of the device can be made compact and thin.

According to the aforesaid preferred embodiment, the small sized video camera is used as a small-sized camera but another small-sized TV camera may also be used. In addition, the image projected by the mirror is captured by the small-sized camera, displayed in the liquid crystal panels, and the image projected at the liquid crystal panels is reversed again by the mirror. However, the external image may be captured by a small-sized camera, projected with a liquid crystal panel and directly seen without reflecting it through a mirror.

As described above, according to the present invention, since the small-sized camera for taking an image of the liquid crystal panel is arranged at the position corresponding to the height position of each of the eyeballs in the main body of the device, the image taken by the small-sized camera and projected onto the liquid crystal panel can be projected directly onto the retina of the eyeballs through the spot light source and thus a clear image can be obtained independent of the viewer's eyesight.

What is claimed is:

1. An eyesight auxiliary device including in a main body of the device a spot light source; transparent liquid crystal panels illuminated by said light source; and convex lenses substantially arranged integral with said liquid crystal panels, in which said main body of the device is installed at a user's head and an image of said liquid crystal panels is directly projected onto a respective retina of each of the eyeballs through said spot light source characterized in that a small-sized camera for taking the image of said liquid crystal panels is arranged at the position corresponding to the height positions of the eyeballs in said main body of the device.

2. An eyesight auxiliary device according to claim 1 in which an image reflected by a mirror surface is taken by said small-sized camera, said image is projected to the liquid crystal panel, and the image of said liquid crystal panel is reflected at the mirror surface and projected onto the retina of the eyeballs.

3. An eyesight auxiliary device according to claim 2 in which a mirror surface for reflecting an image taken by said small-sized camera and another mirror surface for reflecting an image of said liquid crystal panel are composed of one mirror.

4. An eyesight auxiliary device according to claim 1 in which an external image is taken by said small-sized camera, said image is projected by the liquid crystal panel, and the image of said liquid crystal panel is projected onto the retina of the eyeballs.

5. An eyesight auxiliary device according to claim 1 in which said small-sized camera is composed of an infra-red ray camera.

6. An eyesight auxiliary device according to claim 1 in which an image/sound input terminal is provided, said liquid crystal panels are driven by image signals inputted from said terminal and the head-phones are driven by the sound signal.

* * * * *